United States Patent [19]

Carlos

[11] 4,198,285

[45] Apr. 15, 1980

[54] OXIDATION OF HYDROCARBON WAXES IN THE PRESENCE OF SULFOBETAINES

[75] Inventor: Donald D. Carlos, Grayson, Ky.

[73] Assignee: Ashland Oil, Inc., Ashland, Ky.

[21] Appl. No.: 2,088

[22] Filed: Jan. 9, 1979

Related U.S. Application Data

[63] Continuation-in-part of Ser. No. 918,131, Jun. 22, 1978.

[51] Int. Cl.$^2$ .................. C07C 27/10; C09F 7/02; C07C 27/16
[52] U.S. Cl. .................................. 208/3; 260/406; 260/451
[58] Field of Search .................. 260/406, 451; 208/3

[56] References Cited

U.S. PATENT DOCUMENTS

| | | | |
|---|---|---|---|
| 2,338,634 | 1/1944 | Fuchs | 260/451 |
| 2,664,436 | 12/1953 | Heinrich | 208/3 X |
| 2,892,860 | 6/1959 | Pier | 260/451 |
| 3,803,137 | 4/1974 | Egan | 260/585 B |

*Primary Examiner*—John F. Niebling
*Attorney, Agent, or Firm*—Van D. Harrison, Jr.

[57] ABSTRACT

Hydrocarbon waxes are oxidized to high acid numbers by agitating the liquid hydrocarbon wax with a sulfobetaine while forcing gaseous air or oxygen through the liquid charge.

10 Claims, No Drawings

OXIDATION OF HYDROCARBON WAXES IN THE PRESENCE OF SULFOBETAINES

NATURE OF THE INVENTION

This invention relates to the oxidation of hydrocarbon waxes. More particularly, it is concerned with a process for oxidizing hydrocarbon waxes to produce useful oxygenated products.

PRIOR ART

Oxidized petroleum fractions including waxes and petrolatums have, in the past, been employed as the source of saponifiable material in the production of lubricating greases and in the formulation of protective coatings. The oxidates employed for these purposes have been obtained by oxidizing selected petroleum fractions under controlled conditions such that the oxidation proceeds only to a limited extent.

Oxidation of petroleum fractions by the above described method had, associated with it, certain difficulties. Some petroleum fractions are not easily oxidized by the prior art processes and even though oxidizable, in some instances, require a preliminary induction period before the rate of oxidation becomes appreciable. Another problem associated with oxidizing petrolatums is the discoloration of the final wax product rendering it aesthetically unattractive for use in some formulations.

OBJECT OF THE INVENTION

One object of this invention is to provide an improved process for the oxidation of petrolatums. Another object of the invention is to provide a process for oxidizing petrolatums more easily than has heretofore been possible.

SUMMARY OF THE INVENTION

Briefly stated, this invention comprises a process for oxidizing hydrocarbons comprising blowing through a molten mixture of hydrocarbon wax an oxidizing gas in the presence of a minor amount of a sulfobetaine or mixture thereof.

The oxidation is conducted under suitable conditions of gas flow, pressure and temperature to oxidize the hydrocarbon wax to a predetermined acid number.

DESCRIPTION OF THE INVENTION

The sulfobetaines used in the process of this invention may be represented by the structural formula:

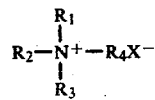

wherein $R_1$ is a high molecular alkyl radical having from 10 to 18 carbon atoms or the amido radical $RCONH(CH_2)_3$ wherein R is a higher alkyl radical of 10 to 18 carbon atoms. $R_2$ and $R_3$ are each alkyl radicals having from about 1 to 3 carbon atoms. $R_4$ is an alkylene or hydroxyalkylene radical having from 1 to 4 carbon atoms, and X is an $SO_3$ radical. $R_1$ and R may be a mixture of a high molecular weight alkyl radical and may contain one or more intermediate linkages such as ether or polyether linkages or non-functional substituents such as hydroxyl or halogen radicals. Examples of sulfobetaines useful herein include coco dimethyl sulfopropyl betaine, stearyl dimethyl sulfopropyl betaine, lauryl bis-(2 hydroxypropyl) sulfopropyl betaine and the like, amido betaines and amidosulfobetaines, wherein the $RCONH(CH_2)_3$ radical is attached to the nitrogen atom of the betaine.

A preferred sulfobetaine is coco dimethylsulfopropyl betaine. Ordinarily, the sulfobetaine is added in a concentration of between 0.2 and 2 parts by weight per 100 parts of hydrocarbon wax. Generally, the sulfobetaine will be in the form of an aqueous solution.

The hydrocarbons useful in this process are the conventional feedstocks previously used as oxidizer feedstock. Ordinarily, said feedstock comprises a mixture of saturated hydrocarbons having an average number of carbon atoms per molecule of 20 to 100. A particular characteristic of some feedstocks is the high concentration of nitrogen present in the molecular structure of some of the hydrocarbons making up the feedstock. The presence of nitrogen appears to inhibit the initiation of the oxidation of the hydrocarbons to their corresponding acids when blown with air.

Accordingly it may be desirable to add a promoting agent to overcome this initial inhibition of oxidation and to initiate the oxidation process.

I prefer to add as an oxidation promoter a quaternary ammonium compound having the formula:

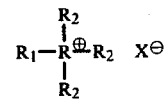

where $R_1$ is an aliphatic hydrocarbon radical of 10 or more carbon atoms, $R_2$ is an aliphatic hydrocarbon radical of 1 to 12 carbon atoms, and $X^\ominus$ is chloride, bromide, iodide, sulfate, or bisulfate.

Although a number of quaternary compounds are deemed suitable for the promoter catalyst in the process of this invention, preferred promoters are dodecyltrimethylammonium chloride or a mixture of quaternary compounds having the formula:

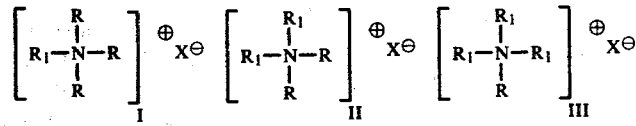

wherein R collectively represents the alkyl residue of a primary alcohol mixture composed of 30–70 wt. percent of (a) straight-chain $C_{16}$–$C_{22}$ alcohols and correspondingly from 70–30 wt. percent fo (b) $C_8$–$C_{15}$ Oxo alcohols consisting essentially of a mixture of straight-chain and single methyl branched isomers, said (a) and (b) being in relative proportions so that from about 95–80 wt. percent of said $R_1$ groups are straight-chain alkyl and correspondingly from 5–20 percent are said branched alkyl, R is a $C_1$–$C_3$ alkyl group, X represents a chloride, bromide or iodide anion, and wherein said mixture of quaternaries is essentially composed of 0–10 wt. percent of compounds of Formula I, 60-85 wt. percent of compounds of Formula II, and 5-25 wt. percent of compounds of Formula III, said mixture being prepared by ammonolysis of a mixture of the corresponding $R_1OH$ alcohols and subsequent quaternization of the ammonolysis product.

The preparation and composition of these quaternary compounds is disclosed in U.S. Pat. No. 3,803,137 which is hereby incorporated by reference. The quaternary compound is added to the hydrocarbon fraction in a minor amount, preferably in a concentration of between 0.5 and 2 parts by weight per 100 parts of hydrocarbon.

Ordinarily, the process will be carried out as a batch process. Air or another oxidizing gas is forced through the reaction mixture of hydrocarbon, sulfobetaine and quaternary compound, if the latter is used, at a rate of between 0.5 and 10 liters (measured at 760 mm of mercury and 25° C.) per liter of hydrocarbon per minute at a temperature of between 150° and 180° C. Ordinarily, the temperature will rise as the oxidation proceeds so that only minimal heat may be required for the oxidation. The oxidation process is conducted at a pressure of between 50 and 400 psig (4.4–28.2 atmospheres). The process is discontinued when a desired acid number is reached. The term "acid number" is defined to mean the number of milligrams of potassium hydroxide required to neutralize 1 gram of sample.

The following example represents the best mode of conducting the process of this invention known to applicant at the date of filing this application.

EXAMPLE I

A number of air oxidations were conducted in laboratory tests using a 1 liter Parr bomb. In each test, the reactor charge amounted to approximately 500 cc of hydrocarbon. To the hydrocarbon material was added the weights of sulfobetaine, (in a 28–30% solution in water) shown in the accompanying table. For comparison purposes runs were also made in which no sulfobetaine was added. The feedstocks studied included both slack waxes and petrolatum samples. The reaction conditions were approximately three hours for each reaction at a temperature of approximately 320° F. (160° C.), a pressure of 200 psig (14.6 atmosphere), and an air input rate of 3.8 liters of air (measured at 25° C. and 1 atmosphere) per liter of reactor charge per minute. Acid number determinations were made at the end of each three-hour run. The results are shown in Table I. Table I also shows the acid numbers obtained when the same hydrocarbon materials were oxidized under the same conditions in the absence of sulfobetaine.

BATCH AIR OXIDATION OF HYDROCARBONS WITH AND WITHOUT ADDITION OF SULFOBETAINE

| RUN NO. | HYDRO-CARBON TYPE | PARTS BY WT. OF SULFO-BETAINE PER 100 PARTS HYDROCARBON | ACID NUMBER |
|---|---|---|---|
| 1-A | (1) | 0.15/99.85 | 37.7 |
| 1-B | (1) | 0/100 | 2.4 |
| 2-A | (2) | 0.15/99.85 | 47.7 |
| 2-B | (2) | 0/100 | 2.4 |
| 3-A | (3) | 0.45/99.55 | 36.3 |
| 3-B | (3) | 0/100 | 0.7 |

(1)Slack wax derived from a mixture of 250N Iranian Rostam and Louisiana sweet crude
(2)Slack wax derived from a mixture of 100N Iranian Rostam and Louisiana sweet crude
(3)petrolatum From a comparison of Runs 1-A, 2-A and 3-A in which the sulfobetaine was added with Runs 1-B, 2-B and 3-B in which sulfobetaine was absent indicates that without the addition of the sulfobetaine no oxidation of the hydrocarbons would have resulted.

I claim:

1. A process for oxidizing liquid hydrocarbon waxes and petrolatums comprising blowing an oxidizing gas through the liquid mass of said hydrocarbon in the presence of a sulfobetaine of the formula:

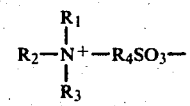

wherein $R_1$ is an alkyl radical having from 10 to 18 carbon atoms or an amido radical of the formula $RCONH(CH_2)_3$ wherein R is an alkyl radical of 10 to 18 carbon atoms, $R_2$ and $R_3$ are each alkyl radicals of 1 to about 3 carbon atoms, and $R_4$ is an alkylene or hydroxyalkylene or hydroxyalkylene radical of about 1 to about 4 carbon atoms.

2. The process of claim 1 wherein said sulfobetaine is coco dimethyl sulfopropyl betaine.

3. The process of claim 1 wherein said betaine is stearyl dimethyl sulfopropyl betaine.

4. The process of claim 1 wherein said sulfobetaine is lauryl bis-(2 hydroxyethyl) sulfopropyl betaine.

5. The process of claim 1 wherein the concentration of sulfobetaine is between about 0.2 and about 2 parts by weight per 100 parts of liquid hydrocarbon.

6. The process of claim 1 wherein said liquid mass of hydrocarbon also contains as an oxidation promoter a quaternary ammonium compound having the formula:

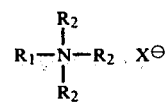

where $R_1$ is an aliphatic hydrocarbon radical of 10 or more carbon atoms, $R_2$ is an aliphatic hydrocarbon radical of 1 to 12 carbon atoms, and $X^\ominus$ is chloride, bromide, iodide, sulfate or bisulfate.

7. The process of claim 6 wherein said quaternary compound is selected from the group consisting of dodecyltrimethylammonium chloride and a mixture of quaternary compounds having the formula:

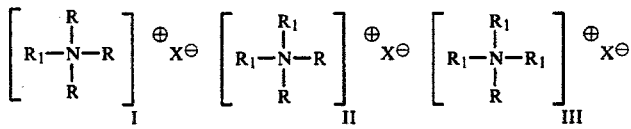

wherein R collectively represents the alkyl residue of a primary alcohol mixture composed of 30–70 wt. percent of (a) straight-chain $C_{16}$–$C_{22}$ alcohols and correspondingly from 70–30 wt. percent of (b) $C_8$–$C_{15}$ Oxo alcohols consisting essentially of a mixture of straight-chain and single methyl branched isomers, said (a) and (b) being in relative proportions so that from about 95–80 wt. percent of said $R_1$ groups are straight-chain alkyl and correspondingly from 5–20 wt. percent are said branched alkyl, R is a $C_1$–$C_3$ alkyl group, X represents a chloride, bromide or iodide anion, and wherein said mixture of quaternaries is essentially composed of 0 to 10 wt. percent of compounds of Formula I, 60–85 wt. percent of compounds of Formula II, and 5–25 wt. percent of compounds of Formula III, said mixture being prepared by ammonolysis of a mixture of the corresponding $R_1OH$ alcohols and subsequent quaternization of the ammonolysis product.

8. The process of claim 6 wherein said quaternary ammonium compound is present in a concentration of between about 0.5 and about 2 parts by weight per 100 parts of liquid hydrocarbon.

9. The process of claim 1 wherein said liquid hydrocarbon wax or petrolatum has an average of between about 20 and about 100 carbon atoms per molecule, said sulfobetaine is coco dimethyl sulfopropyl betaine present in an amount of between about 0.2 and about 2 parts by weight of liquid hydrocarbon wax or petrolatum, said oxidizing gas is forced through said liquid wax or petrolatum at a rate of between 0.5 and 10 liters (measured at 760 mm of mercury and 25° C.) of gas per liter of hydrocarbon per minute at a temperature of between about 150° and 180° C.

10. The process of claim 9 wherein said liquid hydrocarbon wax or petrolatum also contains between about 0.5 and 2 parts by weight of a quaternary ammonium compound.

* * * * *

UNITED STATES PATENT AND TRADEMARK OFFICE
CERTIFICATE OF CORRECTION

PATENT NO. : 4,198,285

DATED : April 15, 1980

INVENTOR(S) : Donald D. Carlos

It is certified that error appears in the above-identified patent and that said Letters Patent are hereby corrected as shown below:

In Column 1, after the title and before the heading, "NATURE OF THE INVENTION" insert --

This application is a continuation-in-part of my copending application, Serial No. 918,131 filed June 22, 1978. --

Signed and Sealed this

Second Day of September 1980

[SEAL]

*Attest:*

SIDNEY A. DIAMOND

*Attesting Officer*     *Commissioner of Patents and Trademarks*